United States Patent
Jones

(10) Patent No.: US 7,780,645 B2
(45) Date of Patent: Aug. 24, 2010

(54) METHOD OF DELIVERING EMBOLIC PARTICLES TO AN ANEURYSM

(75) Inventor: Donald K. Jones, Dripping Springs, TX (US)

(73) Assignee: Codman & Shurtleff, Inc., Raynham, MA (US)

(*) Notice: Subject to any disclaimer, the term of this patent is extended or adjusted under 35 U.S.C. 154(b) by 212 days.

(21) Appl. No.: 11/663,675

(22) PCT Filed: Oct. 26, 2005

(86) PCT No.: PCT/US2005/038993

§ 371 (c)(1),
(2), (4) Date: Mar. 22, 2007

(87) PCT Pub. No.: WO2006/047748

PCT Pub. Date: May 4, 2006

(65) Prior Publication Data

US 2008/0103477 A1 May 1, 2008

Related U.S. Application Data

(60) Provisional application No. 60/622,575, filed on Oct. 26, 2004.

(51) Int. Cl.
*A61M 31/00* (2006.01)
*A61K 9/50* (2006.01)

(52) U.S. Cl. ............. 604/507; 604/508; 604/28; 424/501

(58) Field of Classification Search ........... 604/507, 604/508

See application file for complete search history.

(56) References Cited

U.S. PATENT DOCUMENTS

| | | | |
|---|---|---|---|
| RE31,272 E * | 6/1983 | Pevsner | 604/28 |
| 5,830,178 A | 11/1998 | Jone et al. | |
| 5,947,977 A * | 9/1999 | Slepian et al. | 606/108 |
| 6,017,977 A * | 1/2000 | Evans et al. | 523/113 |
| 6,024,754 A | 2/2000 | Engelson | |
| 6,315,709 B1 * | 11/2001 | Garibaldi et al. | 600/12 |
| 6,530,934 B1 * | 3/2003 | Jacobsen et al. | 606/157 |
| 6,565,551 B1 * | 5/2003 | Jones et al. | 604/507 |
| 6,602,261 B2 | 8/2003 | Greene, Jr. et al. | |
| 6,645,167 B1 * | 11/2003 | Whalen et al. | 604/28 |
| 6,689,089 B1 * | 2/2004 | Tiedtke et al. | 604/43 |
| 7,011,672 B2 * | 3/2006 | Barbut et al. | 606/200 |
| 2003/0185896 A1 * | 10/2003 | Buiser et al. | 424/501 |
| 2003/0223956 A1 * | 12/2003 | Goupil et al. | 424/78.27 |
| 2004/0076582 A1 * | 4/2004 | Dimatteo et al. | 424/1.49 |
| 2004/0101564 A1 | 5/2004 | Rioux et al. | |
| 2004/0167385 A1 | 8/2004 | Rioux et al. | |
| 2004/0225286 A1 * | 11/2004 | Elliott | 606/41 |
| 2005/0085769 A1 * | 4/2005 | MacMahon et al. | 604/96.01 |
| 2007/0150045 A1 * | 6/2007 | Ferrera | 623/1.11 |
| 2008/0103479 A1 * | 5/2008 | Cheng et al. | 604/510 |

* cited by examiner

*Primary Examiner*—Nicholas D Lucchesi
*Assistant Examiner*—Ian K Holloway

(57) ABSTRACT

A method of delivering embolic particles to an aneurysm includes inserting a delivery catheter into the vasculature of a patient and directing the distal end of the delivery catheter to a pre-selected deployment site. Embolic particles are loaded into the delivery catheter, and hydraulic pressure is applied to move the embolic particles through the delivery catheter. The hydraulic pressure is adjusted to control the velocity of the embolic particles and to reduce jetting.

19 Claims, 3 Drawing Sheets

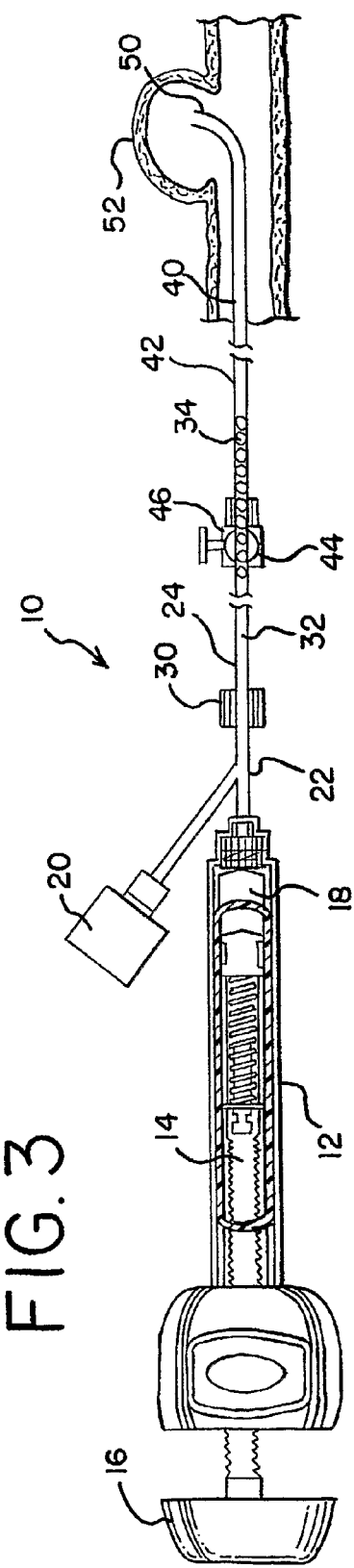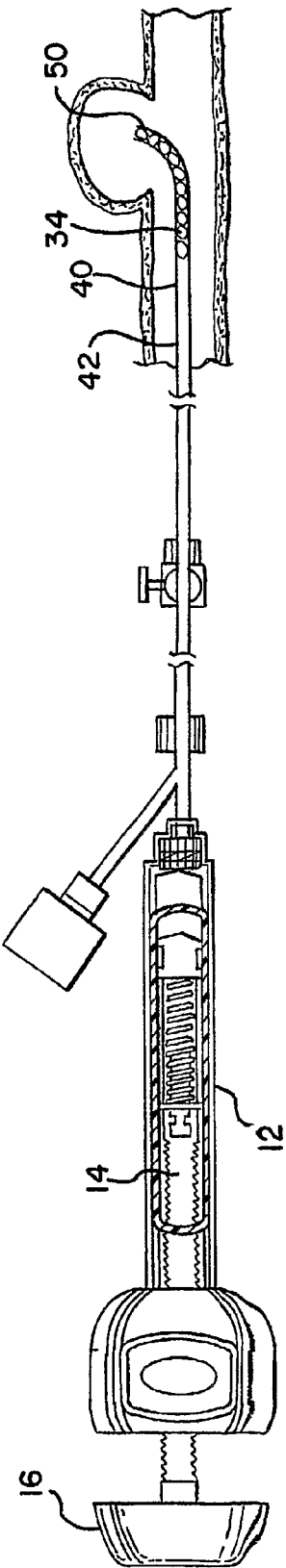

METHOD OF DELIVERING EMBOLIC PARTICLES TO AN ANEURYSM

This application claims priority to provisional application No. 60/622,575 filed on Oct. 26, 2004 which is hereby incorporated herein by reference.

FIELD OF THE INVENTION

The present invention generally relates to medical devices and methods which are used to deploy embolic particles within a vessel of a patient. The present invention is especially suitable for delivering expandable embolic particles to treat vascular abnormalities, such as an aneurysm.

BACKGROUND OF THE INVENTION

Medical devices that can benefit from the present invention include those that are introduced endoluminally and are used to deploy expandable embolic particles for the purpose of occluding a location of concern within a patient, such as an aneurysm.

An aneurysm is an abnormal bulge or ballooning of the wall of a blood vessel, which most commonly occurs in arterial blood vessels. Aneurysms typically form at a weakened point of a wall of a blood vessel. The force of the blood pressure against the weakened wall causes the wall to abnormally bulge or balloon outwardly. Aneurysms, particularly intracranial or neovascular aneurysms, are a serious medical condition because an aneurysm can apply undesired pressure to areas within the brain. Additionally, there is the possibility that the aneurysm may rupture or burst leading to serious medical complications including mortality.

When a patient is diagnosed with an unruptured aneurysm, the aneurysm is treated in an attempt to prevent the aneurysm from rupturing. Unruptured aneurysms have traditionally been treated by what is known as "clipping." Clipping requires an invasive surgical procedure wherein the surgeon makes incisions into the patient's body to access the afflicted blood vessel. Once the surgeon has accessed the aneurysm, he or she places a clip around the neck of the aneurysm to block the flow of blood into the aneurysm which prevents the aneurysm from rupturing. While clipping may be an acceptable treatment for some aneurysms, there is a considerable amount of risk involved with employing the clipping procedure to treat intracranial aneurysms because such procedures require open brain surgery.

More recently, intravascular catheter techniques have been used to treat intracranial aneurysms because such techniques do not require cranial or skull incisions, i.e., these techniques do not require open brain surgery. Typically, these techniques involve using a catheter to deliver embolic devices to a preselected location within the vasculature. For example, in the case of an intracranial or neovascular aneurysm, methods and procedure, which are well known in the art, are used for inserting the distal end of a delivery catheter into the vasculature of a patient and guiding the catheter through the vasculature to the site of the intracranial aneurysm. A vascular occlusion device is then attached to the end of a pusher member which pushes the occlusion device through the catheter and out of the distal end of the catheter where the occlusion device is delivered into the aneurysm.

Once the occlusion device has been deployed within the aneurysm, the blood clots on the occlusion device and forms a thrombus. The thrombus forms an occlusion which seals off the aneurysm, preventing further ballooning or rupture. The deployment procedure is repeated until the desired number of occlusion devices are deployed within the aneurysm. Typically, it is desired to deploy enough coils to obtain a packing density of about 20% or more, preferably about 35% and more if possible.

The most common vascular occlusion device is an embolic coil. Embolic coils are typically constructed from a metal wire which has been twisted into a helical shape. One of the drawbacks of embolic coils is that they do not provide a large surface area for the blood to clot. Additionally, the embolic coil may be situated in such a way that there are relatively considerable gaps between adjacent coils in which blood may freely flow. The addition of extra coils into the aneurysm does not always solve this problem because deploying too many coils into the aneurysm has the potential to lead to an undesired rupture.

Another endoluminal approach for treating an aneurysm is to use a delivery catheter to deliver expandable embolic particles into the aneurysm. Upon deployment, the embolic particles expand to fill in the aneurysm and block off blood flow into the aneurysm. Typically, the embolic particles in the expanded state have a larger cross-sectional extent than that of the delivery catheter. The embolic particles are compressed to fit within the delivery catheter, and the delivery catheter constrains the embolic particles, keeping the embolic particles in the compressed state as the embolic particles travel through the delivery catheter. The friction created by the compressed embolic particles contacting the inner wall of the delivery catheter makes it very difficult, if not impossible, to move the embolic particles through the delivery catheter with the use of a pusher element. Typically the movement of such embolic particles is effected by hydraulic forces, i.e., applying fluid pressure to the embolic particles to move them through and out of the delivery catheter.

The use of hydraulic pressure to move embolic particles creates at least two problems. First, after the first embolic particle has been extruded from the distal end of the catheter, the pressure required to extrude the second embolic particle is lessened, and the pressure required to extrude the third embolic particle is less than the pressure to extrude the second embolic particle and so on. Therefore, under prior approaches, the velocity of each embolic particle extruded becomes faster and faster as delivery proceeds. This can create a dangerous situation wherein the later extruded embolic particles exit the delivery catheter at undesirably high velocities. Traveling at such undesired higher velocities, the extruded embolic particles have the potential to cause damage when contacting the already weakened wall of the vessel.

Another problem with the use of hydraulic pressure is "jetting." "Jetting" refers to the force and speed at which the fluid exits the distal end of the delivery catheter, as well as the volume of fluid that exits the delivery catheter. A small amount of jetting occurs as both the embolic particles and fluid exit the delivery catheter; however, the jetting that occurs after the last embolic particle has exited the distal end of the catheter is of concern because as the last embolic particle exits the delivery catheter there is a release of a large amount of pressure from the catheter into the location of deployment. This release pressure results in a relatively large volume of fluid rapidly entering the deployment site with an undesired force being applied to the already damaged walls of the vessel. In the case of an aneurysm, a large jetting force has a potential catastrophic consequence of rupturing the aneurysm.

Therefore, there remains a need that is recognized and addressed according to the present invention for embolic particle delivery systems and methods for delivering embolic particles in order to allow control of the velocity of the embolic particles, and decreases or limits the effects from jetting and decreases the volume of fluid that is introduced from the catheter into the deployment site.

SUMMARY OF THE INVENTION

The present invention generally relates to embolic particle delivery systems and methods for delivering embolic particles to a location of concern within a vessel. The embolic particle delivery system includes an introducer cartridge in which the embolic particles are compressed and loaded. A fluid filled syringe is connected to a proximal end portion of the introducer cartridge, and the syringe is activated to send the fluid into the introducer cartridge and purge any air in the syringe or introducer cartridge. The introducer cartridge is then connected to a proximal end of catheter which has a distal end that is located at a site of deployment within a patient.

The syringe is then activated to apply hydraulic pressure through the introducer to move the embolic particles from the introducer cartridge into the delivery catheter. Preferably, the embolic particles contain a radiopaque material which allows the movement of the embolic particles to be viewed under fluoroscopy or via other technology. The syringe is activated to apply sufficient hydraulic pressure to move the embolic particles through the catheter to the distal portion. As the embolic particles approach the distal end portion of the catheter, the speed of the embolic particles and the hydraulic pressure are monitored. If necessary, the pressure being applied to move the mass of embolic particles is reduced to slow the speed of the embolic particles. As the embolic particles begin to exit the distal end portion of the catheter, the force required to move the remaining embolic particles is reduced, and the hydraulic pressure imparted to the embolic particles is reduced so that each embolic particle exits the catheter at approximately the same speed.

Therefore, it is an object or aspect of the present invention to provide a method for delivering embolic particles that reduces the amount of jetting upon deployment of the embolic particles.

It is also an object or aspect of the present invention to provide a method for delivering embolic particles that reduces the volume of fluid that is introduced into the deployment site after the embolic particles have been deployed.

It is also an object or aspect of the present invention to provide an embolic particles delivery system that delivers embolic particles while reducing jetting and the volume of fluid introduced into the deployment site.

It is also an object or aspect of the present invention to provide a method of delivering embolic particles that reduces the risk of aneurysm rupture during deployment.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 3 is a partially sectioned view of the embolic particle delivery system of FIG. 1 show with the embolic particles moved into the delivery catheter;

FIG. 4 is a partially sectioned view showing the delivery system of FIG. 1 with the distal end located within an aneurysm of a blood vessel;

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The embolic particle delivery system of the present invention is especially suited for the deployment of expandable embolic particles delivered into an aneurysm. The embolic particles preferably have an expanded cross-sectional extent that is larger than the cross-sectional extent of the lumen of a delivery catheter. Such expandable embolic particles are compressed to fit within a lumen of the delivery catheter for movement therethrough. The expandable embolic particles are preferably made from a porous hydrated polyvinyl alcohol foam gel, but also may be made from any other suitable porous material, such as a biocompatible, macroporous, hydrophilic hydrogel foam material.

One of the factors that determines the compressibility of the expandable embolic particles is the amount of porosity. In general, the larger the porosity of the embolic particle, the more compressible the embolic particle. For example, an embolic particle that has an expanded cross-sectional extent of about 2 mm (2000 microns) can be compressed to about 0.75 mm (750 microns). The same sized embolic particle having a lesser porosity may only be compressible to a cross-sectional extent of about 1.0 mm (1000 microns), and the same sized embolic particle having a greater porosity may be compressible to a cross-sectional extent of about 0.5 mm (500 microns). Preferably, the compressed size or cross-sectional extent of the embolic particle is approximately equal to the size or cross-sectional extent of the lumen of the delivery catheter. Thus, the expanded size and the compressed size of the embolic particles depend on the intended application and the size of the delivery catheter. The expandable embolic particles can have an expanded size or cross-sectional extent that is as great as 10,000 microns, and typically, the expanded cross-sectional extent is not greater than about 5,000 microns, and preferably, not greater that about 3,000 microns. More preferably, the expanded cross-sectional extent ranges from about 45 microns to about 2000 microns.

Figure 1:
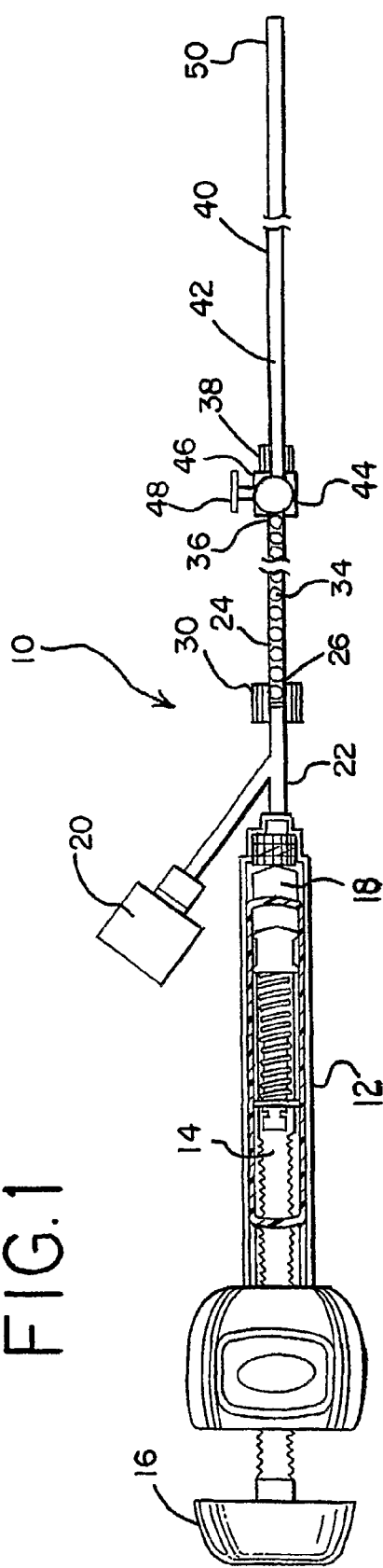
FIG. 1 is a partially sectioned view of an embodiment of an embolic particle delivery system of the present invention.

FIG. 1 illustrates an embolic particle delivery system in accordance with the present invention. The delivery system generally designated as 10 includes a hydraulic injector or syringe 12. The syringe 12 includes a threaded piston 14 which is controlled by handle 16 for infusing fluid within location or compartment 18 into the rest of the system. Typical fluid is saline solution. Preferably, the delivery system 10 includes a pressure gauge 20 for monitoring the hydraulic pressure within the system. Illustratively, the pressure gauge 20 is connected to a distal end portion 22 of the syringe 12. The pressure gauge 20 may be any suitable pressure gauge such as a pressure gauge having mechanical needle display or a computerized gauge having a digital display. Additionally, the pressure gauge 20 may be located at any other suitable location along the system.

Figure 2:
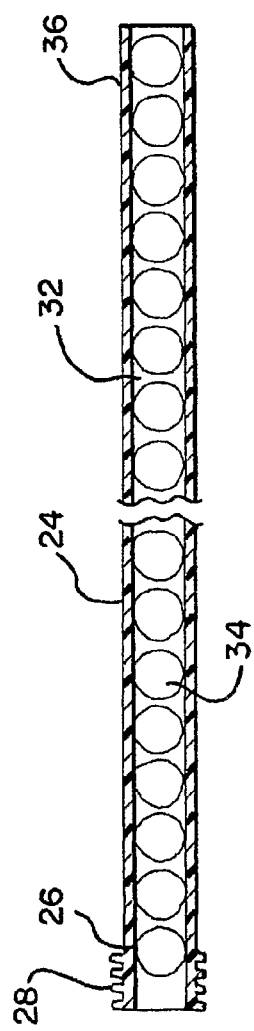
FIG. 2 is a partially sectioned view of an embodiment of an introducer cartridge of the present invention loaded with embolic particles.

Referring to FIGS. 1 and 2, an introducer cartridge 24 has proximal end portion 26 which mates with the distal end portion 22 of the syringe 12. In the illustrated embodiment, the proximal end portion 26 of the introducer cartridge 24 includes threads 28 which mate with a threaded connector 30 located on the distal end portion 22 of the syringe 12. The introducer cartridge 24 is preferably a flexible tubular member having an inner lumen 32. The lumen 32 of the flexible introducer cartridge 24 is adapted to accept and hold expandable embolic particles 34 which have been compressed and, preferably, sequentially loaded into the lumen 32 of the introducer cartridge.

The distal end portion 36 of the introducer cartridge 24 is secured to a proximal end portion 38 of a delivery catheter 40 so that the lumen 32 of the introducer cartridge 24 communicates with the lumen 42 of the delivery catheter 40. Preferably, the distal end portion 36 of the introducer cartridge 24 is secured to the delivery catheter 40 by inserting the distal end portion 36 into an inner channel (not shown) of a valve member 44 of a rotating hemostatic valve 46. The valve member 44 may be rotated by handle 48 to open and close the valve, and thus control the communication between the introducer cartridge 24 and the delivery catheter 40.

To treat an aneurysm, the catheter 40 is inserted into the vasculature of the patient, and the distal end 50 of the delivery catheter is positioned at a preselected location, typically in conjunction with other devices and professional procedures as generally known in the art. As schematically illustrated in FIG. 3, the distal end portion 50 is placed within an aneurysm 52. The catheter 40 is preferably inserted in the vasculature of the patient and positioned before the introducer cartridge is an attached to the catheter, as described below. However, the introducer cartridge may be attached to the catheter before the catheter is inserted into the vasculature. Next, the expandable embolic particles having a larger uncompressed cross-sectional extent than that of the delivery catheter 40 are compressed and loaded into the lumen 32 of the introducer cartridge 24 in a generally known manner. Preferably, the expandable embolic particles are load sequentially, as illustrated in FIG. 2.

After the embolic particles have been loaded, the proximal end portion 22 of the syringe 12 is coupled to the distal end portion 26 of the introducer cartridge 24. The handle 16 of syringe 12 is then used to operate the piston 14 to infuse the fluid in compartment 18 into the lumen 32 of the introducer cartridge 24. Fluid is infused into the introducer cartridge until the syringe 12 and/or the introducer cartridge 24 is purged of any air.

Once the introducer cartridge 24 and the syringe 12 have been purged, the introducer cartridge 24 is inserted into the channel of the valve member 44 of the rotating hemostatic valve 48. The introducer cartridge 24 may then be secured to the delivery catheter 40 by rotating the valve member 44 to a closed position via the handle 48, thereby trapping the distal portion 36 of introducer cartridge 24 between the valve member 44 and the body of the hemostatic valve 46.

The hemostatic valve 46 is then open to allow communication between the lumen 32 of the introducer cartridge 24 and the lumen 42 of the delivery catheter 40. The handle 16 of syringe 12 is then turned to operate the piston 14 of the syringe to apply hydraulic pressure through the introducer cartridge 24 to move the embolic particles 34 into the lumen 42 of the catheter 40, as illustrated in FIG. 3. Sufficient hydraulic pressure is then applied to move the embolic particles 34 through the lumen 42 of the delivery catheter 40, as illustrated in FIG. 4.

Figure 5:
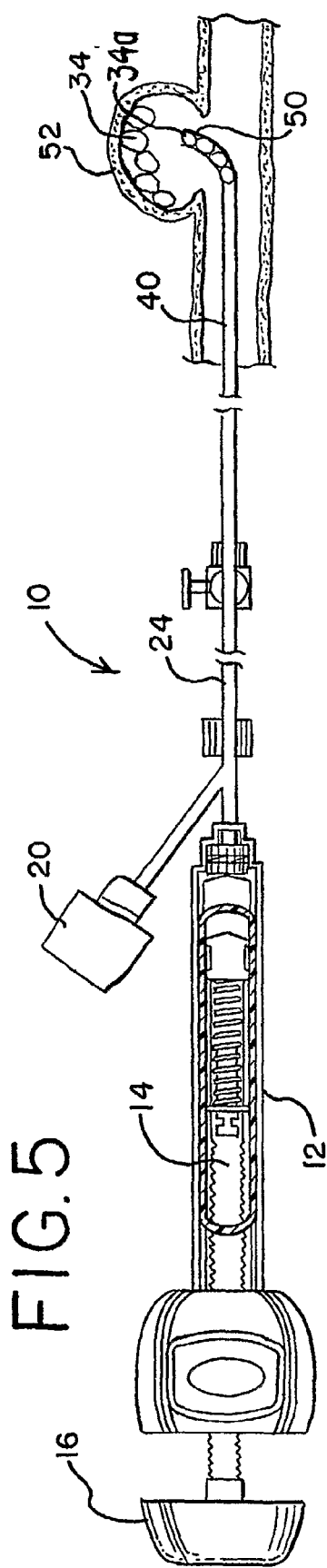
FIG. 5 is a partially sectioned view showing the delivery system of FIG. 1 deploying embolic particles within an aneurysm.

As the embolic particles 34 move through the delivery catheter 40, the location and the speed of the embolic particles 34, and the hydraulic pressure within the delivery system 10 is monitored. Preferably, the embolic particles 34 contain a radiopaque material so that the movement and the speed of the embolic particles 34 may be monitored using fluoroscopy techniques generally known in the art. If it is determined that the velocity of the embolic particles 34 is greater than desired, the handle 16 of the syringe 12 may be turned in the opposite direction to move the piston 14 distally, reducing hydraulic pressure and slowing the velocity of the embolic particles 34. As the embolic particles 34 begin to exit the distal end portion 50 of the catheter into the aneurysm 52, as illustrated in FIG. 5, the force required to move each subsequent embolic particle 34a is reduced. The operator monitoring the speed of the embolic particles and the hydraulic pressure within the delivery system 10 may then reduce the hydraulic pressure as each subsequent embolic particle 34a exits the distal end 50 of the delivery catheter 40 so that substantially all of the embolic particles 34 exit at substantially the same velocity. If the hydraulic pressure is not lessened after each embolic particle exits the delivery catheter 40, each subsequent embolic particle 34a will exit at a faster velocity potentially creating a dangerous situation.

Figure 6:
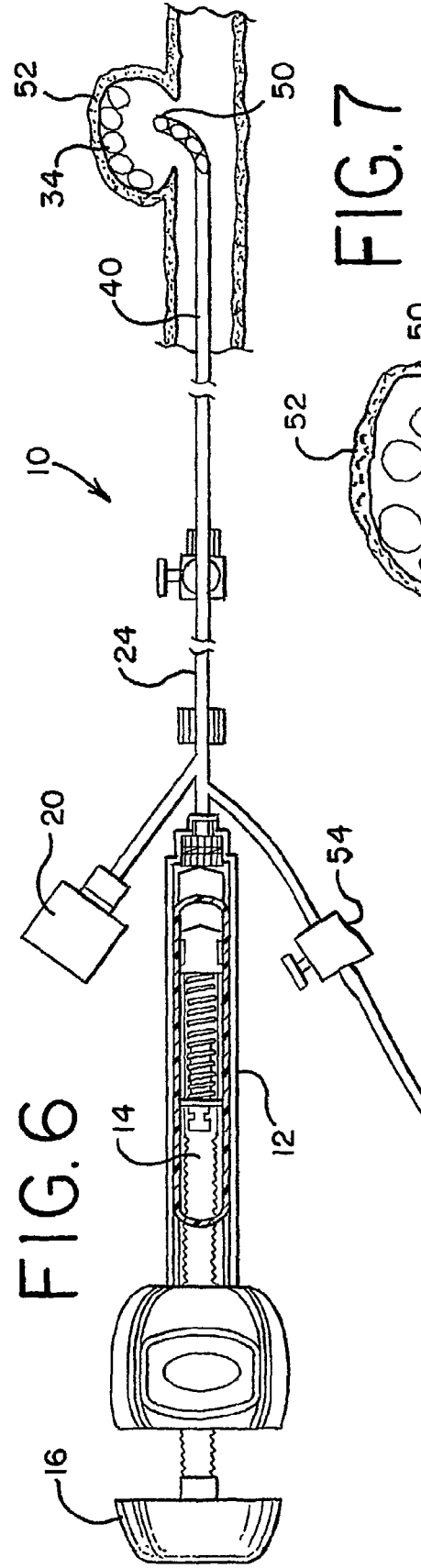
FIG. 6 is a partially sectioned view showing an alternate embodiment of the present invention with the distal end located within an aneurysm.

After the last embolic particle has exited the delivery catheter, the operator may radically reduce hydraulic pressure so as to reduce jetting forces and the volume of fluid that is introduced into the aneurysm. The pressure may be reduced through use of the syringe 12, or through the use of a release valve 54, as illustrate in FIG. 6. It is contemplated that the fluid injector, pressure monitor and release valve could be linked to a computer or control system which monitors and controls the operation of each device. For example, the computer or control system could monitor the hydraulic pressure within the delivery system and control the fluid injector to change the pressure within the system as conditions change. Furthermore, the computer or control system could monitor the pressure within the system and be programmed to activate the release valve at certain pressure; for example, if the pressure exceeds a certain threshold, or after detection of a drop in pressure upon the exiting of the last embolic particle from the delivery catheter.

Figure 7:
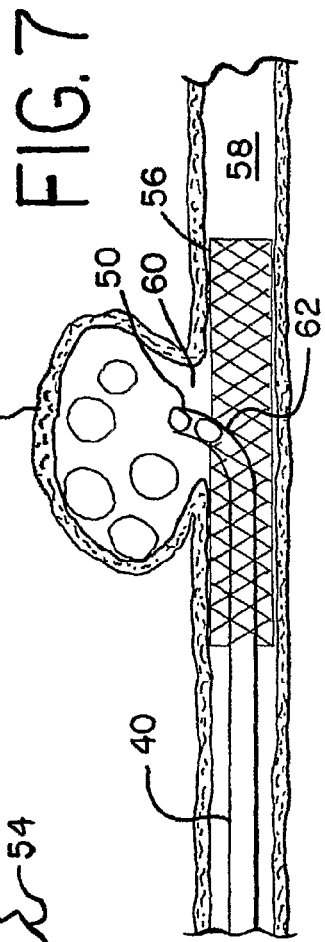
FIG. 7 is a partially sectioned view of an embolic delivery system of the present invention used in conjunction with another embolic element.

The embolic particle deployment system could be used in conjunction with other embolic devices. For example, as illustrated in FIG. 7, an embolic stent 56 could be placed in the vessel 58 so that the embolic stent 56 covers the neck 60 of the aneurysm 52. The distal end portion 50 of the delivery catheter 40 can then be placed through an opening 62 in the stent 56 to access the aneurysm 52 and deliver the embolic particles 34, in a method substantially similar to the method described above.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A method of deploying embolic particles within a patient, comprising:
    inserting a delivery catheter having a proximal end portion and a distal end portion into the vasculature of a patient;
    directing the distal end of the delivery catheter to a preselected site within the vasculature;
    loading embolic particles into the delivery catheter;
    applying hydraulic pressure to the embolic particles to move the embolic particles through the delivery catheter and out of the distal end of the delivery catheter into the preselected site;
    monitoring a velocity of the embolic particles;
    monitoring the hydraulic pressure being applied to the embolic particles; and
    adjusting the hydraulic pressure to control the velocity of the embolic particles.

2. The method according to claim 1 wherein the inserting of the embolic particles comprises compressing expandable embolic particles to fit within the delivery catheter.

3. The method according to claim 1 wherein applying hydraulic pressure comprises activating a fluid filled syringe connected to the delivery catheter to infuse fluid into the delivery catheter.

4. The method according to claim 3 wherein the adjusting of hydraulic pressure comprises employing the fluid filled syringe to adjust hydraulic pressure.

5. The method according to claim 1 wherein the monitoring of the velocity of the embolic particles comprises employing fluoroscopy techniques.

6. The method according to claim 1 wherein the monitoring of hydraulic pressure comprises using a pressure gauge.

7. The method according to claim 1 further comprising rapidly releasing hydraulic pressure from the delivery catheter if the hydraulic pressure exceeds a selected threshold pressure.

8. The method according to claim 1 further comprising rapidly releasing hydraulic pressure from the delivery catheter upon exiting of a last embolic particle from the delivery catheter.

9. The method according to claim 1 wherein the adjusting of the hydraulic pressure comprises incrementally lowering hydraulic pressure after each embolic particle exits the delivery catheter.

10. The method according to claim 1 wherein the adjusting of the hydraulic pressure comprises adjusting the hydraulic pressure so that each embolic particle exits the delivery catheter at substantially the same velocity.

11. A method of deploying expandable embolic particles within the vasculature of a patient, comprising:
    inserting a delivery catheter having a proximal end portion and a distal end portion into the vasculature of a patient;
    directing the distal end of the catheter to a preselected site within the vasculature;
    loading a plurality of expandable embolic particles into an introducer having a proximal end portion and a distal end portion;
    attaching a fluid injector to the proximal end portion of the introducer;
    attaching the distal end of the introducer to the proximal end portion of the delivery catheter;
    applying hydraulic pressure to the embolic particles by injecting fluid from the fluid injector into the introducer so that the embolic particles move from the introducer into the delivery catheter and out of the distal end of the delivery catheter into the pre-selected site;
    monitoring a velocity of the embolic particles;
    monitoring the hydraulic pressure applied to the embolic particles; and
    adjusting the hydraulic pressure to control the velocity of the embolic particles.

12. The method according to claim 11 wherein attaching a fluid injector comprises attaching a fluid-filled syringe.

13. The method according to claim 12 wherein the adjusting of hydraulic pressure comprises employing the fluid filled syringe to adjust hydraulic pressure.

14. The method according to claim 11 wherein the monitoring of the velocity of the embolic particles comprises employing fluoroscopy techniques.

15. The method according to claim 11 wherein the monitoring of hydraulic pressure comprises using a pressure gauge.

16. The method according to claim 11 further comprising rapidly releasing hydraulic pressure from the delivery catheter if the hydraulic pressure exceeds a selected threshold pressure.

17. The method according to claim 11 further comprising rapidly releasing hydraulic pressure from the delivery catheter upon exiting of a last embolic particle from the delivery catheter.

18. The method according to claim 11 wherein the adjusting of the hydraulic pressure comprises incrementally lowering hydraulic pressure after each embolic particle exits the delivery catheter.

19. The method according to claim 11 wherein the adjusting of the hydraulic pressure comprises adjusting the hydraulic pressure so that each embolic particle exits the delivery catheter at substantially the same velocity.

* * * * *